United States Patent
Haddad et al.

(10) Patent No.: US 10,732,100 B2
(45) Date of Patent: Aug. 4, 2020

(54) SYSTEMS AND METHODS FOR PREDICTING SUN PROTECTION FACTOR OF SUNSCREEN FORMULATIONS IN VITRO

(71) Applicant: L'OREAL, Paris (FR)

(72) Inventors: Michael Haddad, Clichy (FR); Benjamin Askenazi, Clichy (FR); Loic Tran, Clichy (FR); Alice Brosselard, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/024,296

(22) Filed: Jun. 29, 2018

(65) Prior Publication Data

US 2020/0003683 A1 Jan. 2, 2020

(51) Int. Cl.
*G01N 21/33* (2006.01)
*G01N 21/64* (2006.01)

(52) U.S. Cl.
CPC ........... *G01N 21/33* (2013.01); *G01N 21/643* (2013.01); *G01N 2021/6439* (2013.01); *G01N 2021/6491* (2013.01)

(58) Field of Classification Search
CPC ................. G01N 21/33; G01N 21/643; G01N 2021/6491; G01N 2021/6439
USPC ........................................................ 250/372
See application file for complete search history.

(56) References Cited

U.S. PATENT DOCUMENTS

| | | | |
|---|---|---|---|
| 5,691,158 A | 11/1997 | Reece et al. | |
| 5,808,307 A * | 9/1998 | Suzuki | G01J 1/429 |
| | | | 250/372 |
| 9,750,326 B2 | 9/2017 | Yoshida et al. | |
| 9,963,271 B2 * | 5/2018 | Richter | G01J 1/50 |
| 10,082,423 B2 * | 9/2018 | Gatto | G01J 1/429 |
| 10,213,007 B2 * | 2/2019 | Lucet-Levannier | A45D 44/005 |
| 10,258,243 B2 * | 4/2019 | LeBoeuf | A61B 5/0205 |
| 2002/0077677 A1 * | 6/2002 | Beck | A61B 5/0059 |
| | | | 607/88 |
| 2008/0248571 A1 | 10/2008 | Amano et al. | |
| 2008/0265170 A1 * | 10/2008 | Ales | A61B 5/0059 |
| | | | 250/372 |
| 2011/0059016 A1 * | 3/2011 | Ramanujam | A61B 5/0059 |
| | | | 424/9.1 |
| 2013/0157261 A1 * | 6/2013 | Sharpe | G01N 21/6428 |
| | | | 435/6.1 |
| 2015/0086955 A1 * | 3/2015 | Poniatowski | G06T 7/0014 |
| | | | 434/267 |
| 2015/0253301 A1 | 9/2015 | Dueva-Koganov et al. | |

(Continued)

FOREIGN PATENT DOCUMENTS

| | | |
|---|---|---|
| EP | 1892517 A2 | 2/2008 |
| EP | 3219302 A1 | 9/2017 |
| WO | 2017186903 A1 | 11/2017 |

OTHER PUBLICATIONS

International Search Report and Written Opinion, dated Aug. 27, 2019, for International Patent Application No. PCT/EP2019/064218. (13 pages).

*Primary Examiner* — David P Porta
*Assistant Examiner* — Gisselle M Gutierrez
(74) *Attorney, Agent, or Firm* — Christensen O'Connor Johnson Kindness PLLC

(57) ABSTRACT

Systems and methods for predicting a Sun Protection Factor (SPF) in vitro, such as by spectral/image analysis, of a sunscreen formulation are described.

12 Claims, 5 Drawing Sheets

(56) References Cited

U.S. PATENT DOCUMENTS

| | | | |
|---|---|---|---|
| 2015/0338272 A1* | 11/2015 | Rastegar | G01J 1/0271 |
| | | | 250/372 |
| 2016/0025481 A1 | 1/2016 | Stanfield et al. | |
| 2016/0051149 A1* | 2/2016 | Viator | A61B 5/445 |
| | | | 600/407 |
| 2017/0249436 A1* | 8/2017 | Miller | G06F 19/326 |
| 2018/0344180 A1* | 12/2018 | Yuan | A61B 5/7214 |
| 2019/0072562 A1* | 3/2019 | Vinegoni | G01N 21/6408 |
| 2019/0125258 A1* | 5/2019 | Miller | A61B 5/4848 |

* cited by examiner

SYSTEMS AND METHODS FOR PREDICTING SUN PROTECTION FACTOR OF SUNSCREEN FORMULATIONS IN VITRO

SUMMARY

In an aspect, the present disclosure provides a system for generating an ultraviolet (UV) absorption analysis generally including a skin tissue phantom impregnated with a marker configured to absorb UV light and generate a detectable signal in response to absorbing the UV light; an interrogator configured to generate interrogation data based on the detectable signal generated by the marker in response to the UV light absorbed by the marker; and an analyzer communicatively coupled to the interrogator and configured to receive the interrogation data from the interrogator, wherein the analyzer is configured to generate the UV absorption analysis based at least in part on the interrogation data.

In another aspect, the present disclosure provides method of generating a UV absorption analysis of a sunscreen formulation generally including receiving, by an analyzer from an interrogator, interrogation data generated by the interrogator, the interrogation data based at least in part on detectable signal generated by a marker impregnated in a skin tissue phantom in response to the marker absorbing UV light; wherein at least a portion of the skin tissue phantom is coated with the sunscreen formulation, and generating, by the analyzer, the UV absorption analysis of the sunscreen formulation based at least in part on the interrogation data.

This foregoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1:
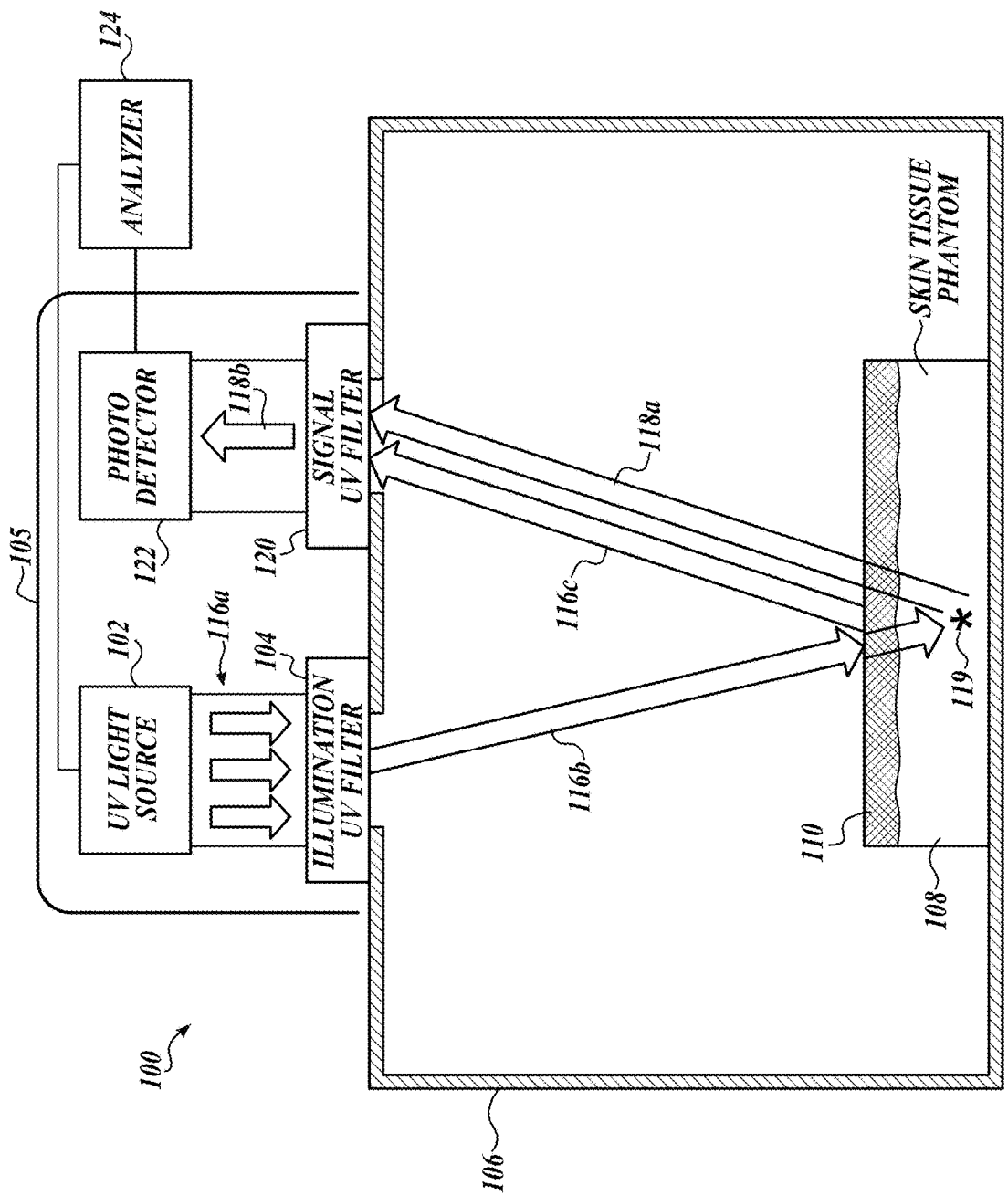
FIG. 1 illustrates a system in accordance with an embodiment of the disclosure.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

The present disclosure generally relates to systems and methods for determining in vitro a sun protection factor ("SPF").

With instances of skin cancer and other skin-related afflictions increasing, awareness about skin protection has also increased. Skin protection often comes in the form of sunscreen formulations, such as sunscreen lotions, sunscreen sprays, sunscreen pastes, and the like. Skin protection can limit or prevent harm to skin from certain kinds of exposure, such as exposure to ultraviolet (UV) electromagnetic energy (e.g., sunlight), which has a wavelength in a range from 10 nm to 400 nm. However, many individuals do not understand the strength of their chosen form(s) of skin protection, and remain vulnerable to exposure when they believe that they are protected.

Existing ratings of skin treatments are imperfect metrics of skin protection. In the United States, sunscreen skin treatments are given an SPF value. The SPF value is intended as a measure of the fraction of sunburn-producing UV rays that reach the skin (e.g., a sunscreen formulation given an "SPF 30" rating indicates that 1/30th of sunburn-producing UV rays reach the skin treated with the sunscreen formulation). However, this reading is imprecise for a number of reasons. In this regard, in vivo testing of SPF includes applying a sunscreen formulation to the skin of a volunteer and measuring how long it takes before sunburn occurs when exposed to a sunlight source. In one example, the amount of exposure to UV rays that produces sunburns varies from individual to individual. In another example, the amount of protection provided by any skin treatment varies based on the amount and uniformity of application of the skin treatment to the skin. In another example, visible skin damage is typically caused by UV radiation type B (UVB), which has a wavelength in the range of 280 nm to 315 nm, and SPF values are based on visible damage caused to skin. However, nonvisible damage to skin is caused by exposure to other sources of electromagnetic radiation, such as UV radiation type A (UVA), which has a wavelength in the range of 315 nm to 400 nm, other UV electromagnetic radiation, or non-UV electromagnetic radiation. Thus, some skin treatments may have high SPF values, indicating that they protect well against UVB, while offering little to no protection from UVA or other forms of electromagnetic radiation.

Conventional in vitro methods of determining are performed on rigid, smooth plates, such as poly(methylmethacrylate) plates, coated with a sunscreen formulation to be tested with local measurement of the UV absorbance of the sunscreen formulation. Such conventional in vitro methods using rigid, smooth plastic plates do not represent how sunscreen formulations and UV filters dispersed or dissolved therein absorb in and aggregate on skin including surface inhomogeneities, particularly as skin stretches, compresses, moves, folds, and the like.

Based on these considerations, there is a need for systems and methods for in vitro testing of sunscreen formulations that more accurately reflect how such sunscreen formulations protect skin UV light.

To that end, the following discussion provides examples of, inter alia, systems and methods for generating UV absorption analysis including a skin tissue phantom impregnated with a marker configured to absorb UV light and generate a detectable signal in response to absorbing the UV light. As will be described in more detail below, an amount of detectable signal generated by the skin tissue phantom coated with the sunscreen formulation can be correlated to an amount of UV light absorbed by the sunscreen formulation. In that regard, as will be described in more detail below, detection of the detectable signal can be used to generate a surface SPF for the sunscreen formulation tested. Further, as will be described in more detail below, the skin tissue phantom is similar to skin in many salient ways, such as surface inhomogeneities, stretchiness, compressibility, and the like, such that systems including the skin tissue phantom are configured to more accurately assess a sunscreen formulation's ability to protect actual skin.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. Further, it will be appreciated that embodiments of the present disclosure may employ any combination of features described herein.

Turning to FIG. 1, a system 100 in accordance with an embodiment of the disclosure is illustrated. System 100 includes interrogator 105, skin tissue phantom 108 shown here disposed within interrogator 105, and analyzer 124 shown here communicatively coupled with interrogator 105 and UV light source 102.

Skin tissue phantom 108 is impregnated with a marker 119 configured to absorb UV light and generate a detectable signal in response to absorbing the UV light. In an embodiment, the marker 119 is dispersed within the skin tissue phantom 108. In an embodiment, the marker 119 is in a solid solution with the skin tissue phantom 108. In an embodiment, the marker is photoluminescent.

In an embodiment, the detectable signal includes visible light. In an embodiment, the detectable signal includes near infrared light. In an embodiment, the detectable signal includes infrared light. As discussed further herein, detectable signals can include all signals differentiable from UV light, such as UV scattered off of sunscreen formulation 110.

As shown, skin tissue phantom 108 includes one or more surface inhomogeneities, shown here as a number of waves on a surface of skin tissue phantom 108. In an embodiment, such surface inhomogeneities include wrinkles, pores, dimples, waves, and the like that resemble analogous surface inhomogeneities on skin. In this regard, sunscreen formulation 110 is coated onto skin tissue phantom 108 in way analogous to sunscreen formulation coated onto a portion of skin. Accordingly, system 100 including skin tissue phantom 108 including surface inhomogeneities is configured to assay sunscreen formulations in a way that accounts for skin surface inhomogeneities and, thus, is configured to provide assay results of sunscreen formulations more representative of sunscreen formulation performance on actual skin.

System 100 further includes interrogator 105 configured to generate interrogation data based on the detectable signal generated by the marker 119 in response to the UV light absorbed by the marker 119. In the illustrated embodiment, interrogator 105 includes photo-detection housing 106 shown here housing skin tissue phantom 108, UV light source 102 emitting UV light 116, and a photodetector 122 configured to generate the interrogation data based on the detectable signal. As shown, UV light source 102 and photodetector 122 are communicatively coupled to analyzer 124. UV light source 102 emits illumination UV light 116a. As shown, a portion of illumination UV light 116a passes through illumination UV filter 104 configured to absorb a first portion of the illumination UV light 116a and allow filtered illumination UV light 116b to pass through to the skin tissue phantom 108. In this regard, the system 100 is configured to limit UV light that impinges upon the skin tissue phantom 108, such as limiting the UV light that impinges upon the skin tissue phantom 108 to particular wavelength ranges of UV light. As described further herein with respect to the methods of the present disclosure, by limiting ranges of UV light that impinge upon the sunscreen formulation, a user can selectively assay a sunscreen formulation for UV light absorbance/scattering properties in particular wavelength ranges.

As shown, filtered illumination UV light 116b impinges upon sunscreen formulation 110 and skin tissue phantom 108. A portion of filtered illumination UV light 116b scatters off of sunscreen formulation 110 to provide scattered UV light 116c. Another portion of filtered illumination UV light 116b passes through sunscreen formulation 110 and impinges upon skin tissue phantom 108 including marker 119. As above, marker 119 generates detectable signal 118a in response to absorbing filtered illumination UV light 116b. As discussed further herein, the amount or intensity of detectable signal 118a can be correlated to an efficacy of sunscreen formulation 110 in absorbing, scattering, reflecting, etc. filtered illumination UV light 116b that impinges upon the sunscreen formulation 110. The better the sunscreen formulation 110 is at preventing filtered illumination UV light 116b from reaching the skin tissue phantom 108 the lower the amount and/or intensity of the detectable signal 118a.

In an embodiment, system 100 includes a signal UV filter 120 configured to absorb UV light, such as scattered UV light 116c scattered off of sunscreen formulation 110, and configured allow the detectable signal 118a to pass to photodetector 122. As shown, detectable signal 118a passes through signal UV filter 120 as filtered detectable signal 118b to impinge upon photodetector 122, whereas scattered UV light 116c does not pass through to photodetector 122. In this regard, system 100 is configured to selectively provide filtered detectable signal 118b to photodetector 122, thereby, for example, increasing a signal-to-noise ratio for signals generated by photodetector 122.

Likewise, in an embodiment, photo-detection housing 106 is configured to substantially prevent light from outside of the photo-detection 106 housing other than illumination UV light, such as illumination UV light 116a, from entering an interior of the photo-detection housing 106. In this regard, the photo-detection housing 106 is configured to substantially prevent light from impinging upon photodetector 122 other than filtered detectable signal 118b. Accordingly, signal-to-noise ratios are further improved by isolating the interior of the photo-detection housing 106 from sources of stray light.

Analyzer 124 is communicatively coupled to the interrogator 105 and configured to receive interrogation data, such as data generated by photodetector 122 in response to filtered detectable signal 118b, from the interrogator 105. By improving signal-to-noise ratios in interrogation data generated by the interrogator 105, system 100 is configured to provide a more accurate surface SPF.

Figure 2:
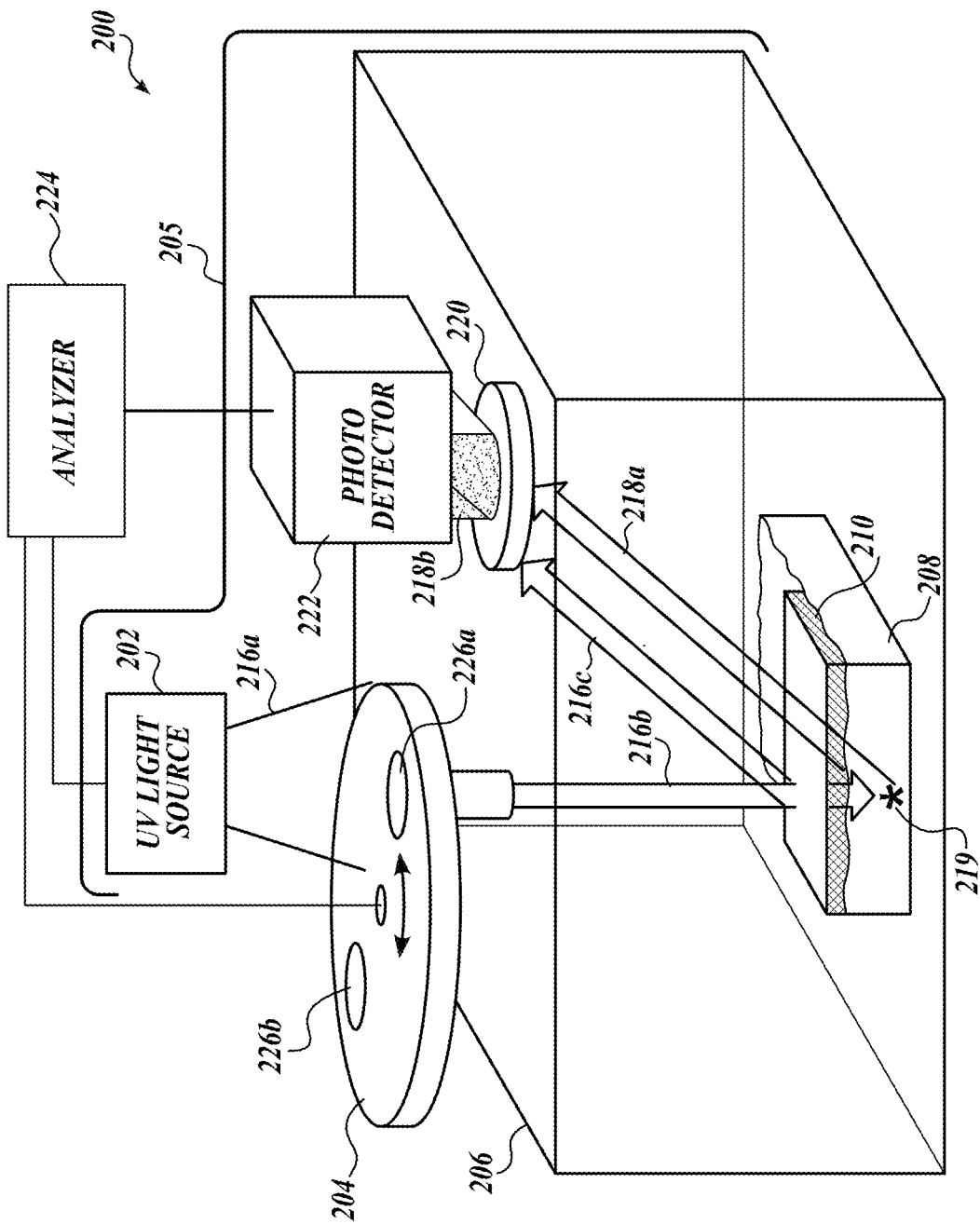
FIG. 2 illustrates another system in accordance with an embodiment of the disclosure.

As above, in an embodiment, the systems described herein are configured to assay sunscreen formulations in particular wavelength ranges. In that regard, attention is directed to FIG. 2 where a system 200 in accordance with an embodiment of the disclosure is illustrated. System 200 includes a skin tissue phantom 208 impregnated with a marker 219, interrogator 205 housing skin tissue phantom 208, and analyzer 224 operatively coupled to interrogator 205.

Interrogator 205 includes photo-detection housing 206; skin tissue phantom 208 shown here disposed within the photo-detection housing 206 and partially coated with sunscreen formulation 210; UV light source 202 configured to emit illumination UV light 216a at least a portion of which impinges upon skin tissue phantom 208; and photodetector 222 configured to generate the interrogation data based on the detectable signal 218a.

In the illustrated embodiment, interrogator 205 further includes an illumination filter wheel 204 including a first illumination filter 226a configured to absorb a first portion of the illumination UV light 216a and allow a second portion of the illumination UV light 216a, (filtered illumination UV light 216b) to pass through to the skin tissue phantom 208. Illumination filter wheel 204 further includes a second illumination UV filter 226b configured to absorb a third portion of the illumination UV light 216a different from the first portion of illumination UV light 216a and allow a fourth portion of the illumination UV light (not shown) different from filtered illumination UV light 216b to pass through to the skin tissue phantom 208.

As shown, first illumination UV filter 226a and second illumination UV filter 226b are disposed on separate portions of the illumination filter wheel 204. Further, illumination filter wheel 204 is operably coupled to analyzer 224, which includes circuitry configured to selectively place one of the illumination UV filters 226a or 226b in the path of illumination UV light 216a. In this regard, the illumination filter wheel 204 is configured to selectively absorb portions of the illumination UV light 216a and allow certain other portions of illumination UV light 216a to pass through to the skin tissue phantom 208. By selectively absorbing certain portions of illumination UV light 216a with the illumination filter wheel 204 and allowing others to pass through to the skin tissue phantom 208 and sunscreen formulation 210, a user can tune illumination UV light 216a reaching marker 219 impregnated in the skin tissue phantom 208 and/or impinging upon the sunscreen formulation 210. In this regard, a user can selectively assay sunscreen formulation 210 at a variety of UV wavelength ranges.

In an embodiment, the marker 219 is one of a plurality of markers impregnated in the skin tissue phantom 208, and wherein each of the plurality of markers is configured to absorb UV light and generate a detectable signal in response to absorbing the UV light, such as filtered illumination UV light 216b. In an embodiment, a first marker of the plurality of markers, such as marker 219, absorbs UV light in a first wavelength range and in response the first marker 219 generates a first detectable signal, such as detectable signal 218a. In an embodiment, a second marker (not shown) of the plurality of markers absorbs UV light in a second wavelength range different from the first wavelength range and the second marker is configured to generate a second detectable signal different from the first detectable signal in response to absorbing UV light in the second wavelength range. In this regard, a user can determine the effectiveness of a sunscreen formulation to absorb, scatter, and the like UV light at two or more different UV light wavelength ranges based at least in part on amounts or intensities of the first and second detectable signals.

Such determinations are useful where, for example, a sunscreen formulation includes, for example, two UV light-absorbing components that absorb UV light in different wavelength ranges. As above, certain sunscreen formulations may protect adequately in a first wavelength range of UV light, such as UVB, but inadequately in a second wavelength range of UV light, such as UVA. Because system 200 is configured to independently assay two or more UV wavelength ranges, system 200 is, for example, suitable to quantitatively assay the ability of a sunscreen formulation to absorb, scatter, etc. both, for example, UVA light and UVB light.

In the illustrated embodiment, interrogator 205 further includes signal UV filter 220 configured to allow detectable signals, such as detectable signal 218a, pass through as filtered detectable signal 218b to photodetector 222. In an embodiment, signal UV filter 220 is further configured to absorb or otherwise prevent UV light, such as scattered UV light 216c, from impinging upon photodetector 222. As discussed further herein with respect to FIG. 1, such filtration of scattered and other UV light improves signal to noise ratios and otherwise improves generation of interrogation data based on detectable signals.

A method of generating a UV absorption analysis in accordance with an embodiment of the disclosure will now be described. In an embodiment, the method includes generating interrogation data based at least in part on a detectable signal generated by a marker impregnated in a skin tissue phantom. As discussed further herein with respect to FIGS. 1 and 2, in an embodiment, the detectable signal is a photoluminescent signal generated by the marker in response to the marker absorbing UV light. In an embodiment the interrogation data is generated by an interrogator, such as interrogators 105 or 205, including, for example, a photodetector, such as photodetectors 122 and 222.

In an embodiment, such interrogation data is received by an analyzer, such as analyzers 124 and 224. The analyzer generates the UV absorption analysis of the sunscreen formulation based at least in part on the interrogation data.

In an embodiment generating the UV absorption analysis of the sunscreen formulation includes determining a transmittance spectrum of the sunscreen formulation. In an embodiment, a transmittance spectrum is a ratio of UV electromagnetic energy, such as UV light, that goes through the sunscreen formulation to the total amount of UV electromagnetic energy impinging upon the sunscreen formulation. As described further herein, by using skin tissue phantoms impregnated with a marker configured to generate a detectable sign in response to absorbing UV light, there is a correlation between the amount and/or intensity of the detectable signal and the illumination UV light. Further, by analyzing the detectable signal generated by the systems described herein, one can estimate a proportion of UV light that passes through a sunscreen formulation coating the skin tissue phantom, rather than being absorbed by, scattered off of, etc. the sunscreen formulation.

Figure 3A:
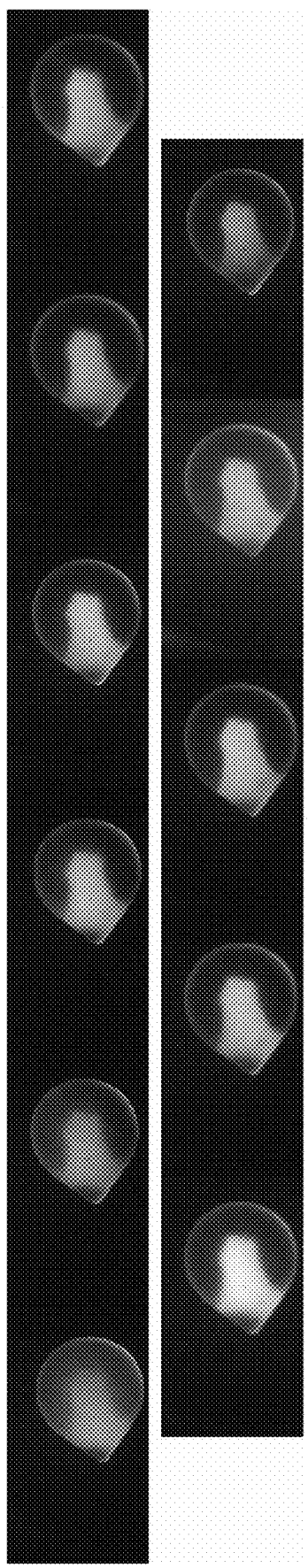
FIG. 3A is a series of images of a skin tissue phantom partially coated with a sunscreen formulation illuminated with UV light at a variety of wavelengths ranges in accordance with an embodiment of the disclosure.

In an embodiment, the transmittance spectrum is determined at a plurality of UV wavelength ranges. In that regard, attention is directed to FIGS. 3A and 3B. FIG. 3A is a series of images of a skin tissue phantom partially coated with a sunscreen formulation illuminated with UV light at a variety of wavelengths ranges, in accordance with an embodiment of the disclosure. As shown in FIG. 3A, the portion of the skin tissue phantom coated with the sunscreen formulation is darker than the portion of the skin tissue phantom not coated with the sunscreen formulation. As above, the portion of skin tissue phantom not coated in the sunscreen formulation generates more detectable signal, here photoluminescent light, than the portion of skin tissue phantom coated with the sunscreen formulation because more UV light reaches the marker in this portion of the skin tissue phantom.

Figure 3B:
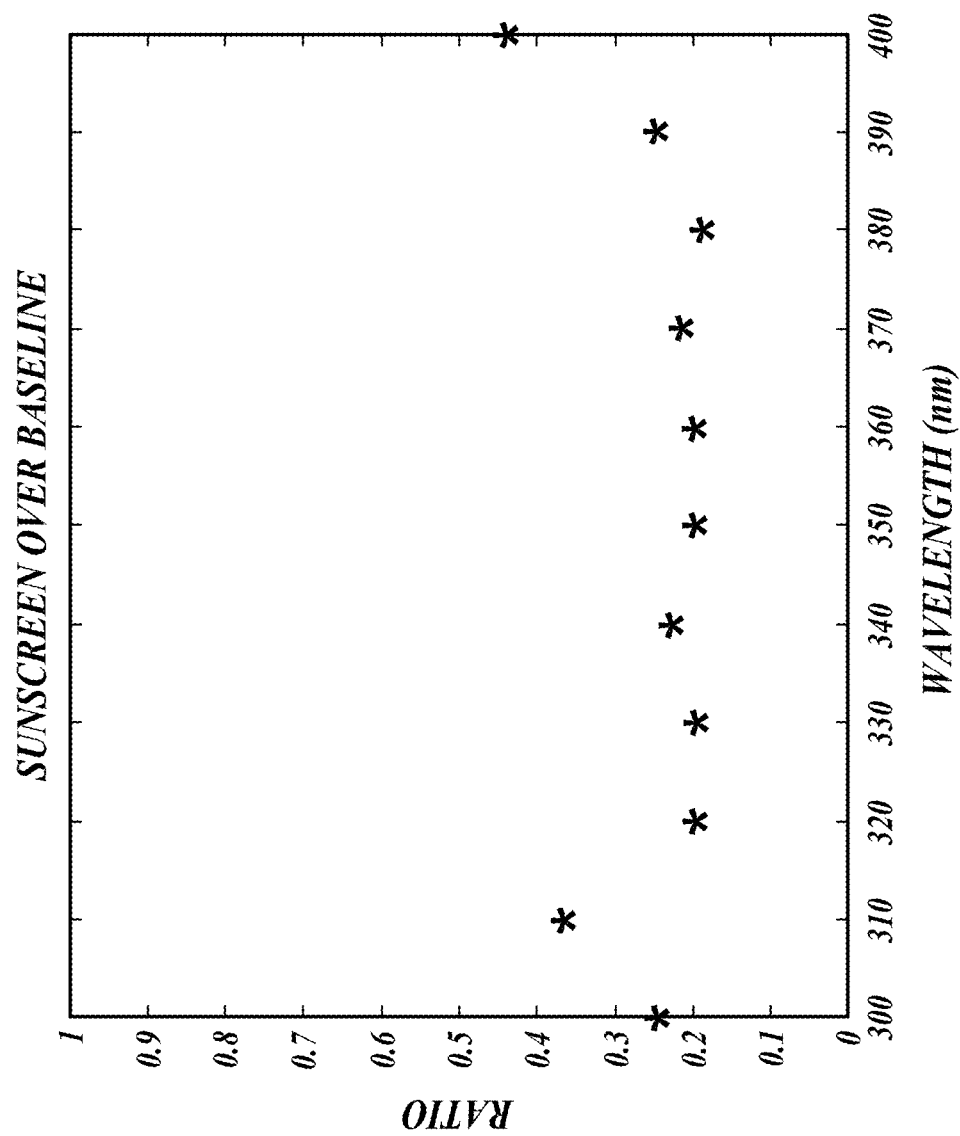
FIG. 3B graphically illustrates a ratio of photoluminescent light emitted by a portion of the skin tissue phantom of FIG. 3A coated by the sunscreen formulation to a portion of the skin tissue phantom not coated by the sunscreen formulation as a function of wavelength in accordance with an embodiment of the disclosure.

FIG. 3B graphically illustrates a ratio of photoluminescent light emitted by a portion of the skin tissue phantom of FIG. 3A coated by the sunscreen formulation to a portion of the skin tissue phantom not coated by the sunscreen formulation as a function of wavelength. In an embodiment, generating the UV absorption analysis includes generating sunscreen formulation interrogation data from a portion of the skin tissue phantom coated by the sunscreen formulation; generating control interrogation data from a portion of the skin tissue phantom not coated by the sunscreen formulation; and taking a ratio of the sunscreen formulation interrogation data and the control interrogation data, such as is shown in FIG. 3B for a variety of wavelengths. In an embodiment, the portion of the skin tissue phantom not coated by the sunscreen formulation is a portion of the skin tissue phantom different from the portion of the skin tissue phantom coated with the sunscreen formulation, as illustrated in FIG. 3A. Alternatively, in an embodiment, generating the transmittance spectrum for a particular wavelength range includes taking a ratio of detectable signal generated by a portion of the skin tissue phantom when it is coated with the sunscreen formulation to detectable signal generated by the same portion of the skin tissue phantom when it is not coated with the sunscreen formulation.

In an embodiment, the transmittance spectrum is determined at a plurality of portions of the skin tissue phantom. Accordingly, in an embodiment, generating the interrogation data includes generating interrogation data at a plurality of portions of the skin tissue phantom with, for example, an imaging sensor including, for example, a plurality of pixels configured to register detectable signals from the plurality of portions of the skin tissue phantom. As discussed further, in an embodiment, the skin tissue phantom includes a plurality of surface inhomogeneities configured to generate an inhomogeneous coating of sunscreen formulation. By generating interrogation data at the plurality of portions of the skin tissue phantom a user can assay how a surface SPF or UV absorbance varies with position of the skin tissue phantom, such as positions including surface inhomogeneities.

In an embodiment, generating the transmittance spectrum includes generating interrogation data at a plurality of wavelengths at a plurality of portions of the skin tissue phantom.

In an embodiment, the UV absorption analysis includes generating a first UV absorption analysis; distressing the skin tissue phantom, such as by stretching, folding, and/or compressing the skin tissue phantom; and generating a second UV absorption analysis of the distressed skin tissue phantom. In this regard, a user can determine the effects, if any, on an ability of a sunscreen formulation to prevent UV light from reaching skin after being stretched, folded, compressed, and the like. Because the skin tissue phantoms of the present disclosure stretch, fold, and compress like skin, the methods described herein are configured to account for, for example, any aggregation, dispersion, etc. of sunscreen formulations that may occur on the skin of a user. This is in contrast to the rigid plastic plates that are conventionally used in in vitro testing of sunscreen formulations, which do not stretch, fold, or compress like skin.

Figure 4:
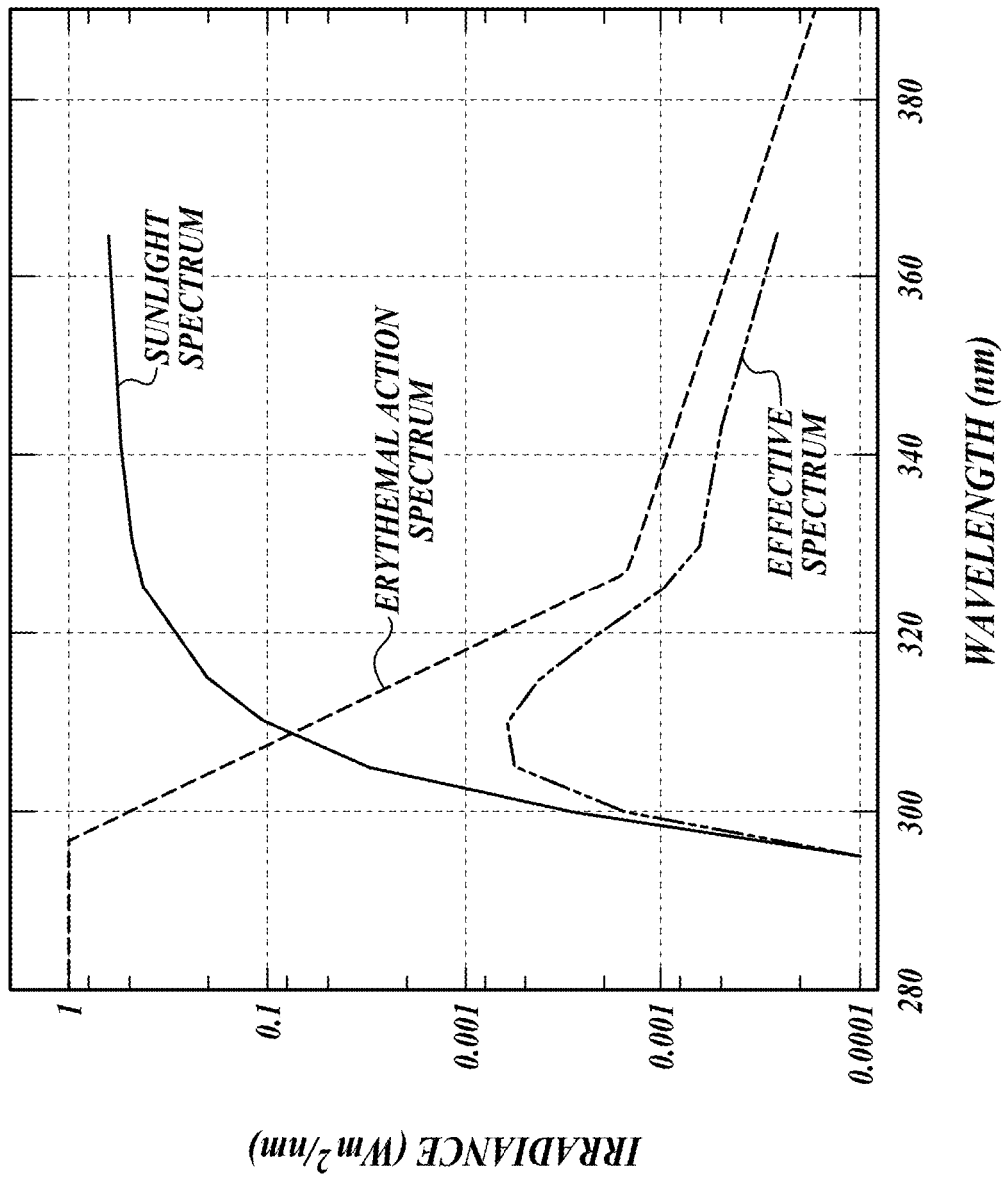
FIG. 4 graphically illustrates sunlight spectrum in terms of irradiance ($W/m^2*nm$) as a function of wavelength with the erythemal action spectrum and the effective spectrum superimposed upon the sunlight light spectrum.

In an embodiment, the UV absorption analysis includes generating a surface SPF of a sunscreen formulation coating at least a portion of a skin tissue phantom as described further herein. In an embodiment, the surface SPF is calculated by the formula:

$$SPF = \frac{\sum E_\lambda S_\lambda \Delta_\lambda}{\sum E_\lambda S_\lambda T_\lambda \Delta_\lambda}$$

where $E_\lambda$ is the erythemal action spectrum (skin sensitivity in the UV range), $S_\lambda$ is the solar irradiance spectrum (standardized solar energy in the UV Range), $T_\lambda$ is the transmittance spectrum of the sunscreen formulation, and $\Delta_\lambda$ is FIG. 4 graphically illustrates sunlight spectrum in terms of irradiance (W/m$^2$*nm) as a function of wavelength with the erythemal action spectrum and the effective spectrum superimposed upon the sunlight light spectrum.

From this formula, SPF can be calculated based upon the transmittance spectrum of the sunscreen formulation, determined by the systems and methods described further herein as a function of wavelength.

Certain embodiments disclosed herein utilize circuitry in order to operably couple two or more components, generate information, determine operation conditions, control an appliance or method, process signals, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, the circuitry of the systems described herein includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The embodiments of the invention in which an exclusive property or privilege is claimed are defined as follow:

1. A system for generating an ultraviolet (UV) absorption analysis comprising: a skin tissue phantom impregnated with a marker configured to absorb UV light and generate a detectable signal in response to absorbing the UV light; an interrogator configured to generate interrogation data based on the detectable signal generated by the marker in response to the UV light absorbed by the marker; and an analyzer communicatively coupled to the interrogator and configured to receive the interrogation data from the interrogator, wherein the analyzer is configured to generate the UV absorption analysis based at least in part on the interrogation data;
    wherein the interrogator includes: a photo-detection housing configured to house the skin tissue phantom within the photo-detection housing; a UV light source configured to emit illumination UV light onto the skin tissue phantom; and a photodetector configured to generate the interrogation data based on the detectable signal;
    wherein the photo-detection housing is configured to prevent light from outside of the photo-detection housing from entering an interior of the photo-detection housing;
    further comprising an illumination UV filter configured to absorb a first portion of the illumination UV light and allow a second portion of the illumination UV light to pass through to the skin tissue phantom.

2. The system of claim 1, a second illumination UV filter configured to absorb a third portion of the illumination UV light different from the first portion of illumination UV light and allow a fourth portion of the illumination UV light different from the second portion of the illumination UV light to pass through to the skin tissue phantom.

3. The system of claim 2, wherein the first illumination UV filter and second illumination UV filter are configured to selectively absorb portions of the illumination UV light.

4. The system of claim 1, further comprising: a signal UV filter configured to absorb UV light and allow the detectable signal to pass to the photodetector.

5. The system of claim 1, wherein the marker is photoluminescent, and wherein the detectable signal includes visible light.

6. The system of claim 1, wherein the marker is one of a plurality of markers impregnated in the skin tissue phantom, and wherein each of the plurality of markers is configured to absorb UV light and generate a detectable signal in response to absorbing the UV light.

7. The system of claim 6, wherein a first marker of the plurality of markers absorbs UV light in a first wavelength range and a second marker of the plurality of markers absorbs UV light in a second wavelength range different from the first wavelength range.

8. The system of claim 7, wherein the first marker is configured to generate a first detectable signal in response to absorbing UV light in the first wavelength range, and wherein the second marker is configured to generate a second detectable signal different from the first detectable signal in response to absorbing UV light in the second wavelength range.

9. The system of claim 1, wherein the skin tissue phantom includes a polysiloxane.

10. The system of claim 1, wherein the skin tissue phantom includes one or more surface inhomogeneities.

11. The system of claim 1, wherein the marker is dispersed within the skin tissue phantom.

12. The system of claim 1, wherein the marker is in a solid solution with the skin tissue phantom.

\* \* \* \* \*